(12) United States Patent
Maeda et al.

(10) Patent No.: US 8,173,804 B2
(45) Date of Patent: May 8, 2012

(54) PROCESS FOR PRODUCTION OF MIRTAZAPINE

(75) Inventors: Chiharu Maeda, Higashiosaka (JP); Takuma Maeda, Fujiidera (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 513 days.

(21) Appl. No.: 12/443,662

(22) PCT Filed: Mar. 13, 2008

(86) PCT No.: PCT/JP2008/054628
§ 371 (c)(1),
(2), (4) Date: Mar. 30, 2009

(87) PCT Pub. No.: WO2008/114691
PCT Pub. Date: Sep. 25, 2008

(65) Prior Publication Data
US 2010/0029934 A1 Feb. 4, 2010

(30) Foreign Application Priority Data
Mar. 22, 2007 (JP) ................................ P2007-075573

(51) Int. Cl.
*C07D 471/14* (2006.01)

(52) U.S. Cl. .................................................. 540/578

(58) Field of Classification Search .................. 540/578
See application file for complete search history.

(56) References Cited

U.S. PATENT DOCUMENTS

| 4,062,848 A | 12/1977 | van der Burg |
| 2002/0065413 A1 | 5/2002 | Maeda et al. |
| 2004/0138447 A1 | 7/2004 | Iishi et al. |

FOREIGN PATENT DOCUMENTS

| JP | 2004-500324 A | 1/2004 |
| WO | WO-00/62782 A1 | 10/2000 |
| WO | WO-01/38329 A1 | 5/2001 |
| WO | WO-01/38330 A1 | 5/2001 |
| WO | WO-2005/005410 A1 | 1/2005 |

OTHER PUBLICATIONS

International Preliminary Report on Patentability dated Oct. 1, 2009 issued in the corresponding International Application No. PCT/JP2008/054628.
Frans M. Kaspersen et al., "The Synthesis of Org 3770 Labelled with $^3$H, $^{13}$C and $^{14}$C", Journal of Labelled Compounds and Radiopharmaceuticals, vol. XXVII, No. 9 Feb. 24, 1989, pp. 1055-1068.

*Primary Examiner* — Brenda Coleman
(74) *Attorney, Agent, or Firm* — Birch, Stewart, Kolasch & Birch, LLP

(57) ABSTRACT

The invention provides a process for production of mirtazapine as a convenient process for obtaining mirtazapine from a reaction mixture obtained by cyclization of 2-(4-methyl-2-phenylpiperazin-1-yl)pyridine-3-methanol with concentrated sulfuric acid, at high purity and in a form suitable for safe use as a drug.

The production process for mirtazapine is characterized in that a reaction mixture obtained by cyclization of 2-(4-methyl-2-phenylpiperazin-1-yl)pyridine-3-methanol with concentrated sulfuric acid is diluted with water, the dilution is alkalinized in the presence of propanol, the mirtazapine is extracted with propanol and the mirtazapine is crystallized from the extract.

7 Claims, No Drawings

PROCESS FOR PRODUCTION OF MIRTAZAPINE

This application is a national stage entry under 35 U.S.C. §371 of PCT/JP2008/054628, filed Mar. 13, 2008.

TECHNICAL FIELD

The present invention relates to a process for production of mirtazapine, which is useful as an antidepressant. More specifically, the invention relates to a process for production of mirtazapine by cyclization of 2-(4-methyl-2-phenylpiperazin-1-yl)pyridine-3-methanol with concentrated sulfuric acid.

BACKGROUND ART

Mirtazapine is a useful antidepressant compound, and it can be synthesized by cyclization of 2-(4-methyl-2-phenylpiperazin-1-yl)pyridine-3-methanol with concentrated sulfuric acid. Known methods for isolating mirtazapine include a method in which the cyclized reaction mixture is diluted with water and then alkalinized, and the produced precipitate is separated and then extracted with methylene chloride and concentrated to obtain crude mirtazapine (Patent document 1); a method in which the cyclized reaction mixture is diluted with water and then alkalinized and extracted in the presence of toluene, concentrated, and crystallized in a toluene-heptane system (Patent document 2); and a method in which the cyclized reaction mixture is diluted with water and then alkalinized, the produced precipitate is separated, the mother liquor is concentrated and both of the obtained residues are combined and suspended in isopropanol, after which extraction and concentration are performed to obtain crude mirtazapine (see Patent document 1).

[Patent document 1] Japanese Patent Public Inspection No. 2004-500324
[Patent document 2] International Patent Publication No. WO 01/038330

DISCLOSURE OF THE INVENTION

Problems to be Solved by the Invention

In the conventional processes, however, it is necessary to separate the precipitate after it is produced upon rendering the cyclized reaction mixture alkaline, and the precipitate is then extracted with methylene chloride, or the reaction mixture is alkalinized in the presence of toluene and extracted. However, the purity of the obtained mirtazapine after concentration is not satisfactory, and therefore recrystallization has been necessary.

Incidentally, according to the Guideline for Residual Solvents published by the International Conference on Harmonisation of Technical Requirements for Registration of Pharmaceuticals for Human Use (ICH) (hereinafter referred to as "ICH Guideline"), methylene chloride and toluene are Class 2 solvents whose residues in pharmaceutical products are to be limited, and it is preferred to avoid the use of such solvents in the final stages of drug manufacturing.

It is an object of the present invention to provide a process for production of mirtazapine as a convenient process for obtaining mirtazapine from a reaction mixture obtained by cyclization of 2-(4-methyl-2-phenylpiperazin-1-yl)pyridine-3-methanol with concentrated sulfuric acid, at high purity and suitable for safe use as a drug.

Means for Solving the Problems

As a result of much research on the problems referred to above, the present inventors have completed this invention after discovering that propanol, which is among the Class 3 solvents with low toxicity according to the ICH Guideline and is miscible with water, can unexpectedly extract mirtazapine from water-diluted reaction mixtures under alkaline conditions.

Specifically, the invention is the following.

[1] A production process for mirtazapine, characterized in that a reaction mixture obtained by cyclization of 2-(4-methyl-2-phenylpiperazin-1-yl)pyridine-3-methanol with concentrated sulfuric acid is diluted with water, the dilution is alkalinized in the presence of propanol, the mirtazapine is extracted with propanol and the mirtazapine is crystallized from the extract.

[2] A production process according to [1] above, wherein the amount of propanol used is 130-500 parts by weight with respect to 100 parts by weight of the 2-(4-methyl-2-phenylpiperazin-1-yl)pyridine-3-methanol.

[3] A production process according to [1] or [2] above, wherein heptane is added after the dilution is alkalinized.

[4] A production process according to [3] above, wherein the amount of heptane used is 10-70 wt % with respect to the total of propanol and heptane.

[5] A production process according to any one of [1] to [4] above, wherein the concentrated sulfuric acid is used at 300-400 parts by weight with respect to 100 parts by weight of the 2-(4-methyl-2-phenylpiperazin-1-yl)pyridine-3-methanol for cyclization, and the obtained reaction mixture is diluted with water at 100-400 parts by weight with respect to 100 parts by weight of the reaction mixture.

[6] A production process according to any one of [1] to [5] above, wherein an alkali metal hydroxide is used for the alkalinization.

[7] A production process according to any one of [1] to [6] above, wherein the reaction mixture that has been diluted with water is decolored at pH 3 or below.

EFFECT OF THE INVENTION

According to the invention, the extraction from the reaction mixture that has been diluted with water is carried out with propanol, which is a Class 3 solvent with low toxicity according to the ICH Guideline, and therefore the obtained mirtazapine can be safely used as a drug.

The extraction with propanol also gives crystals of higher purity than extraction with methylene chloride or toluene, thus eliminating the need for recrystallization.

In addition, since the reaction mixture that has been diluted with water is directly extracted using propanol under alkaline conditions, there is no need for a step of extraction after the mirtazapine precipitate that is produced has been isolated, and therefore the process is greatly simplified.

Moreover, alkalinization after addition of propanol to the water-diluted reaction mixture facilitates dissolution of the mirtazapine precipitate as well.

BEST MODE FOR CARRYING OUT THE INVENTION

The 2-(4-methyl-2-phenylpiperazin-1-yl)pyridine-3-methanol used as the starting material according to the invention can be synthesized by the method described in WO 01/23345 or WO 01/042240, for example.

Mirtazapine (1,2,3,4,10,14b-hexahydro-2-methylpyrazino[2,1-a]pyrido[2,3-c][2]benzazepine; CAS Registry No.: 85650-52-8) is synthesized by cyclization of 2-(4-methyl-2-phenylpiperazin-1-yl)pyridine-3-methanol with concentrated sulfuric acid, as represented by the following formula.

[Chemical Formula 1]

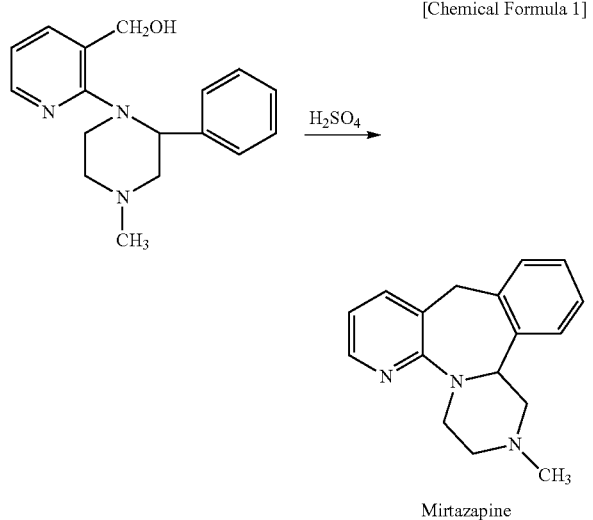

Mirtazapine

The concentrated sulfuric acid used is preferably 97-99% concentrated sulfuric acid.

The amount of concentrated sulfuric acid used will normally be 300-400 parts by weight and is preferably 340-380 parts by weight with respect to 100 parts by weight of the 2-(4-methyl-2-phenylpiperazin-1-yl)pyridine-3-methanol.

The reaction is carried out by addition of 2-(4-methyl-2-phenylpiperazin-1-yl)pyridine-3-methanol to the concentrated sulfuric acid. The temperature of the reaction mixture during addition is usually 0-50° C. and preferably 5-40° C. from the viewpoint of reducing heat release and limiting production of tar-like impurities.

The addition of 2-(4-methyl-2-phenylpiperazin-1-yl)pyridine-3-methanol is preferably carried out in portions (10-30 portions, for example) from the viewpoint of efficiently promoting the reaction.

After addition of the 2-(4-methyl-2-phenylpiperazin-1-yl) pyridine-3-methanol, stirring is effected for 3-10 hours usually at about 20-50° C. and preferably at about 30-40° C., to accelerate the reaction.

Completion of the cyclization reaction can be confirmed by HPLC (high performance liquid chromatography).

Upon completion of the reaction, the sulfuric acid concentration of the reaction mixture is usually lowered by a method such as dropwise addition into water. From the viewpoint of manageability, the amount of water used is preferably 100-400 parts by weight with respect to 100 parts by weight of the reaction mixture. The liquid temperature of the diluent is preferably kept at about 0-30° C., from the viewpoint of reducing heat release and limiting production of impurities (tar).

This is preferably followed by decoloration in order to improve the color tone and increase the purity. The decoloring agent may be decolorizing carbon or the like, and the decoloration may be carried out at 5-35° C. for 10-60 minutes. The decoloring agent is then filtered out and washed with usually 500-600 parts by weight of water with respect to 100 parts by weight of the decoloring agent.

From the viewpoint of safety, the decoloration is preferably carried out after adjusting the pH of the diluent. The pH will usually be no greater than 3, and is preferably 1-2. The present inventors have found, surprisingly, that it is important from the standpoint of increasing the purity for the decoloration to be carried out at no higher than pH 3.

The pH adjustment is accomplished with an alkali. As examples of alkalis there may be mentioned alkali metal hydroxides such as sodium hydroxide and potassium hydroxide, with sodium hydroxide being preferred. The alkali is preferably added dropwise as an aqueous solution, to a concentration of 20-50 wt % and preferably 20-30 wt % from the viewpoint of manageability. The pH adjustment will usually be in a range of 5-50° C. and preferably 10-35° C.

Next, propanol is added to the filtrate and the mixture is alkalinized for extraction of mirtazapine.

It is a feature of the invention that mirtazapine is extracted from an aqueous solution using propanol, which is a solvent of Class 3 with low toxicity according to the ICH Guideline and is normally miscible with water in any proportion, and this allows mirtazapine to be obtained at higher purity and in a safer form for use as a drug, than when the extraction is accomplished with methylene chloride or toluene.

It is another feature of the invention that for the alkalinization and extraction of mirtazapine, propanol is added beforehand to accomplish direct and easier extraction of the mirtazapine from the aqueous solution, thus facilitating dissolution of the mirtazapine precipitate and eliminating the need for a step of extraction after isolation of the mirtazapine precipitate.

The extraction with propanol is possible because the aqueous solution contains a large amount of inorganic salt due to the concentrated sulfuric acid and alkali.

The propanol used may be either 1-propanol or 2-propanol. The amount of propanol used is preferably 130-500 parts by weight, more preferably 130-300 parts by weight and most preferably 130-200 parts by weight with respect to 100 parts by weight of the 2-(4-methyl-2-phenylpiperazin-1-yl)pyridine-3-methanol. If the amount of propanol used is less than 130 parts by weight, the mirtazapine will not dissolve after alkalinization of the reaction mixture, thus preventing liquid separation, while if it is greater than 500 parts by weight, the extract may contain impurities (inorganic salt of the concentrated sulfuric acid and alkali, for example).

Addition of the propanol is followed by alkalinization. The pH will normally be 8 or higher, and is preferably 10-12. The alkali used for this step may be the same alkali used for the aforementioned pH adjustment, and it is preferably added dropwise in the form of an aqueous solution, at a concentration of 20-50 wt % and preferably 20-30 wt % from the viewpoint of manageability. The temperature of the reaction mixture during pH adjustment will usually be 20-50° C.

According to the invention, heptane is preferably added after alkalinization, for extraction with a propanol-heptane mixed solvent. This can minimize carry-in of water into the organic layer and is therefore advantageous for obtaining an anhydrate of mirtazapine, while also shortening the time required for distilling off of the solvent. The amount of heptane used is preferably 10-70 wt % and more preferably 50-70 wt % based on the total weight of the propanol and heptane.

The extraction is carried out while heating the solution at 70-80° C., after which liquid separation is performed to remove the aqueous layer.

Propanol or a propanol/heptane mixed solvent may be added to the organic layer next.

When propanol is added, the amount will normally be 350-1000 parts by weight and preferably 600-950 parts by weight with respect to 100 parts by weight of the 2-(4-methyl-2-phenylpiperazin-1-yl)pyridine-3-methanol.

When a propanol/heptane mixed solvent is added, the amount of heptane is 10-60 wt % with respect to the total of propanol and heptane, and the amount of the mixed solvent is usually 350-1000 parts by weight and preferably 350-700 parts by weight with respect to 100 parts by weight of the 2-(4-methyl-2-phenylpiperazin-1-yl)pyridine-3-methanol.

The solution may be subjected to dehydration treatment, and for example, a dehydrating agent such as anhydrous magnesium sulfate, anhydrous sodium sulfate or molecular sieves may be used.

The amount of dehydrating agent used will normally be 10-20 parts by weight with respect to 100 parts by weight of the 2-(4-methyl-2-phenylpiperazin-1-yl)pyridine-3-methanol.

This may be followed by another decoloration treatment if necessary, for improved color tone or increased purity.

As decoloring agents there may be mentioned active alumina, decolorizing carbon and the like. Alumina A-11 (product of Sumitomo Chemical Co., Ltd.) may be mentioned as an active alumina product. The amount of active alumina used will normally be 5-30 parts by weight and preferably 10-20 parts by weight with respect to 100 parts by weight of the 2-(4-methyl-2-phenylpiperazin-1-yl)pyridine-3-methanol.

Shirasagi A (product of Takeda Pharmaceutical Co., Ltd.) may be mentioned as a decolorizing carbon product. The amount of decolorizing carbon used will normally be 2-10 parts by weight and preferably 4-6 parts by weight with respect to 100 parts by weight of the 2-(4-methyl-2-phenylpiperazin-1-yl)pyridine-3-methanol.

The alumina and decolorizing carbon may be used alone or in combination.

The temperature for decoloration will normally be 15° C.-40° C. and preferably 20-35° C. The time required for decoloration is usually about 15-30 minutes.

The decoloring agent is then filtered and washed with propanol. The amount of propanol used for washing will usually be 200-250 parts by weight with respect to 100 parts by weight as the total decoloring agent.

The propanol or propanol/heptane mixed solvent is then distilled off. The solvent may be distilled off at atmospheric pressure or under reduced pressure. The degree of reduced pressure may be 0.6-40 kPa and preferably 4-30 kPa from the viewpoint of improving the distillation rate.

The solvent is distilled off until the necessarily extent of crystallization occurs. When 2-propanol is used, the solvent is distilled off until the 2-propanol remains in the concentrate at 40-100 parts by weight and preferably 40-80 parts by weight with respect to 100 parts by weight of the 2-(4-methyl-2-phenylpiperazin-1-yl)pyridine-3-methanol. When 1-propanol is used, the solvent is distilled off until the 1-propanol remains in the concentrate at 40-100 parts by weight and preferably 40-60 parts by weight with respect to 100 parts by weight of the 2-(4-methyl-2-phenylpiperazin-1-yl)pyridine-3-methanol.

Crystallization can be carried out directly from the obtained concentrate, or mirtazapine may instead be crystallized from a solvent of Class 3 of the ICH Guideline, water or a mixture thereof. From the viewpoint of stirrability and improved yield, heptane is preferably added for the crystallization. The amount of heptane will normally be 10-100 parts by weight and preferably 40-80 parts by weight with respect to 100 parts by weight of the 2-(4-methyl-2-phenylpiperazin-1-yl)pyridine-3-methanol. In order to ensure stable quality, the temperature during the heptane addition is preferably 55-70° C. which will not cause deposition of the crystals. The heptane is preferably added dropwise.

Seed crystals are preferably added so that the obtained solution has a uniform crystal size. They will usually be added at 48-55° C. The amount of seed crystals used will normally be 0.005-0.1 part by weight with respect to 100 parts by weight of the 2-(4-methyl-2-phenylpiperazin-1-yl)pyridine-3-methanol.

The crystals are then matured at 48-55° C. for about 1-2 hours and cooled. The cooling is preferably gradual cooling, for example at 0-10° C. for 1-10 hours and preferably 5-8 hours.

The mirtazapine crystals are isolated by filtering and washed with heptane or the like. The amount of heptane used may be 30-100 parts by weight with respect to 100 parts by weight of the 2-(4-methyl-2-phenylpiperazin-1-yl)pyridine-3-methanol.

The isolated crystals may be dried under reduced pressure at a temperature of 45-65° C.

This convenient process allows production of mirtazapine at high purity and in a form safe for use as a drug.

EXAMPLES

The invention will now be explained in greater detail by examples, with the understanding that the invention is not limited only to these examples.

TABLE 1

| | | HPLC conditions: | | |
|---|---|---|---|---|
| | Column | Mobile phase | Flow rate | Detector (UV) |
| Conditions | ODS (4.6 × 250 mm) | Phosphate buffer (pH = 4)/ acetonitrile Gradient conditions: 90/10 → 18/82 | 1.0 ml/min | 220 nm |

Example 1

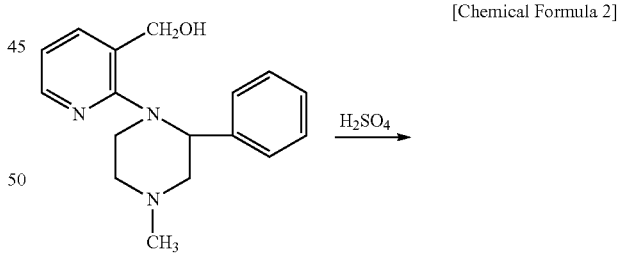

[Chemical Formula 2]

To 530 g (5.4 mol) of 98% sulfuric acid there was added 147.4 g (0.52 mol) of 2-(4-methyl-2-phenylpiperazin-1-yl)pyridine-3-methanol in portions over a period of about 3 hours, under a nitrogen atmosphere at 30-40° C. The mixture was then stirred at 30-40° C. for about 6 hours. Upon confirming disappearance of the starting material by HPLC, an amount of 677 g of reaction mixture was obtained. A 260 g portion of the reaction mixture was added dropwise into 408 g of water at 5-26° C. for dilution. The vessel containing the reaction mixture was washed with 25.5 g of 98% sulfuric acid, and added to the diluent. The pH was adjusted to 1.5 by dropwise addition of 635.8 g of an aqueous solution of 25% sodium hydroxide to the diluent at 13-30° C. After then adding 21 g of decolorizing carbon and stirring at 30-33° C. for 45 minutes, the mixture was filtered and washed with 108 g of water, and the filtrate was separated into 2 parts.

To 699 g of the separated filtrate there was added 51 g of 2-propanol, and then a 25% sodium hydroxide aqueous solution was added dropwise at 30-33° C. to pH 11.2 (53.4 g of solution used). The liquid separation was performed at a temperature of approximately 76° C. After then adding 255 g of 2-propanol to the organic layer, 4.8 g of alumina A-11 (product of Sumitomo Chemical Co., Ltd.) was added, the mixture was stirred at about 28° C. for 15 minutes, and then 1.4 g of decolorizing carbon was added and the mixture was stirred for 15 minutes. The decoloring agent was then filtered out and washed with 14.2 g of 2-propanol. The filtrate was concentrated under reduced pressure and the 2-propanol was distilled off to a concentrated residue of 38.5 g. After then adding 7.5 g of 2-propanol and heating to 66° C., 15 g of heptane was added. A small amount of mirtazapine seed crystals was added at about 53° C., and matured at 50° C. for 1 hour and then cooled to 1° C. over a period of 6 hours. The crystals were filtered out and washed with 14 g of heptane. They were then dried under reduced pressure at about 60° C. to obtain 21.2 g of mirtazapine as white crystals. The yield was 80% and the HPLC purity was 99.98%.

Example 2

To 699 g of the remainder of the filtrate that had been separated into two parts in Example 1 there was added 51 g of 1-propanol, and then a 25% sodium hydroxide aqueous solution was added dropwise at 22-30° C. to pH 11.8 (54.1 g of solution used). The liquid separation was performed at a temperature of approximately 76° C. After then adding 170 g of 1-propanol to the organic layer and cooling to approximately 27° C., 4.8 g of alumina A-11 (product of Sumitomo Chemical Co., Ltd.) was added, the mixture was stirred at about 23° C. for 15 minutes, 1.4 g of decolorizing carbon was added and the mixture was stirred for 15 minutes. After filtration, the decoloring agent was washed with 14.2 g of 1-propanol. The filtrate was concentrated under reduced pressure at approximately 70° C. and the 1-propanol was distilled off to a concentrated residue of 37.1 g. After then adding 1.9 g of 1-propanol and heating, 16 g of heptane was added. A small amount of mirtazapine seed crystals was added at about 48° C. and matured at about 50° C. for 1 hour, and then cooled to 1° C. over a period of 6 hours. The crystals were filtered out and washed with 14 g of heptane. They were then dried under reduced pressure at about 60° C. for 1 hour to obtain 19.6 g of mirtazapine as white crystals. The yield was 73.9% and the HPLC purity was 99.97%.

Example 3

To 102 g (1.04 mol) of 98% sulfuric acid there was added 28.3 g (0.1 mol) of 2-(4-methyl-2-phenylpiperazin-1-yl)pyridine-3-methanol in portions over a period of about 4 hours, under a nitrogen atmosphere at approximately 40° C. The mixture was then stirred at approximately 40° C. for 5 hours. Disappearance of the starting material was confirmed by HPLC. The reaction mixture was added dropwise into 204 g of water for dilution. The vessel containing the reaction mixture was washed with 13 g of 98% sulfuric acid, and added to the diluent. The pH was adjusted to 1-2 by dropwise addition of an aqueous solution of 25% sodium hydroxide to the diluent at 13-30° C. After then adding 10 g of decolorizing carbon and stirring at 30-31° C. for 40 minutes, the mixture was filtered and washed with 54 g of water.

To the filtrate there was added 37 g of 2-propanol, and then a 25% sodium hydroxide aqueous solution was added dropwise at 25-35° C. to pH 11 (62 g of solution used). After next adding 57 g of heptane, liquid separation was performed at a temperature of about 70° C. To the organic layer there were added 99 g of 2-propanol and 15 g of heptane, and then 5 g of alumina A-11 (product of Sumitomo Chemical Co., Ltd.) was added, 1.4 g of decolorizing carbon was further added and the mixture was stirred at about 30° C. for 15 minutes. The decoloring agent was then filtered out and washed with 14 g of 2-propanol. The filtrate was concentrated under atmospheric pressure to a concentrated residue of 38.2 g. A small amount of mirtazapine seed crystals was added at about 53° C. and matured for 2 hours, and then cooled to about 1° C. The crystals were filtered out and washed with 14 g of heptane. They were then dried under reduced pressure at about 60° C. to obtain 21.2 g of mirtazapine as white crystals. The yield was 80% and the HPLC purity was 99.98%.

INDUSTRIAL APPLICABILITY

According to the invention it is possible to conveniently produce mirtazapine from a reaction mixture obtained by cyclization of 2-(4-methyl-2-phenylpiperazin-1-yl)pyridine-3-methanol with concentrated sulfuric acid, at high purity and in a form suitable for safe use as a drug.

The invention claimed is:

1. A production process for mirtazapine, characterized in that a reaction mixture obtained by cyclization of 2-(4-methyl-2-phenylpiperazin-1-yl)pyridine-3-methanol with concentrated sulfuric acid is diluted with water, the dilution is alkalinized in the presence of propanol, the mirtazapine is extracted with propanol and the mirtazapine is crystallized from the extract.

2. A production process according to claim 1, wherein the amount of propanol used is 130-500 parts by weight with respect to 100 parts by weight of the 2-(4-methyl-2-phenylpiperazin-1-yl)pyridine-3-methanol.

3. A production process according to claim 1, wherein heptane is added after the dilution is alkalinized.

4. A production process according to claim 3, wherein the amount of heptane used is 10-70 wt % with respect to the total of propanol and heptane.

5. A production process according to claim 1, wherein the concentrated sulfuric acid is used at 300-400 parts by weight with respect to 100 parts by weight of the 2-(4-methyl-2-phenylpiperazin-1-yl)pyridine-3-methanol for cyclization, and the obtained reaction mixture is diluted with water at 100-400 parts by weight with respect to 100 parts by weight of the reaction mixture.

6. A production process according to claim 1, wherein an alkali metal hydroxide is used for the alkalinization.

7. A production process according to claim 1, wherein the reaction mixture that has been diluted with water is decolored at pH 3 or below.

* * * * *